United States Patent [19]

Novak

[11] Patent Number: 5,716,210

[45] Date of Patent: Feb. 10, 1998

[54] DISPOSABLE FILTER FOR DENTAL HANDPIECE

[75] Inventor: Eugene J. Novak, Deerfield, Ill.

[73] Assignee: Dentsply Research & Development Corp., Milford, Del.

[21] Appl. No.: 176,112

[22] Filed: Dec. 29, 1993

[51] Int. Cl.⁶ .............................. A61C 1/10; A61C 1/12; A61C 17/02
[52] U.S. Cl. .................................................. 433/82; 433/80
[58] Field of Search ........................ 433/80, 81, 82, 433/84, 85, 86, 87, 88; 210/445, 446, 448, 452, 495; 55/482, 503, 505; 604/405, 406, 252

[56] References Cited

U.S. PATENT DOCUMENTS

| | | | |
|---|---|---|---|
| 1,688,401 | 10/1928 | Slagel | 210/445 |
| 2,502,614 | 4/1950 | Zender | 210/446 |
| 2,641,364 | 6/1953 | Depallens | 55/503 X |
| 2,664,395 | 12/1953 | Marchaad | 210/446 |
| 2,758,597 | 8/1956 | Elder | 604/252 X |
| 2,901,112 | 8/1959 | Naftulin et al. | 210/446 |
| 3,782,083 | 1/1974 | Rosenberg | 210/445 X |
| 3,954,625 | 5/1976 | Michalski | 210/445 |
| 4,367,081 | 1/1983 | Harvey | 210/445 X |
| 4,741,697 | 5/1988 | Herbison | 433/80 |
| 4,950,159 | 8/1990 | Hansen | 433/80 |
| 4,966,550 | 10/1990 | Privat | 433/25 |
| 5,204,004 | 4/1993 | Johnston et al. | 210/651 |
| 5,230,624 | 7/1993 | Wolf et al. | 433/82 |
| 5,286,201 | 2/1994 | Yu | 433/80 |

*Primary Examiner*—Nicholas D. Lucchesi
*Attorney, Agent, or Firm*—Douglas J. Hura; James B. Bieber

[57] ABSTRACT

A filter is provided for a dental device of the type including a hand-held working portion which utilizes air and water and a utility supply portion which supplies air and water to the hand-held working portion through respective air and water conduits therein. The filter comprises a filter body defining an air opening therethrough and a water opening therethrough. The air and water openings are respectively positioned for alignment with corresponding air and water openings of at least one of a hand-held working portion and a utility supply portion. The filter body has a filter medium for filtering air and water passing through the respective air and water openings thereof.

25 Claims, 3 Drawing Sheets

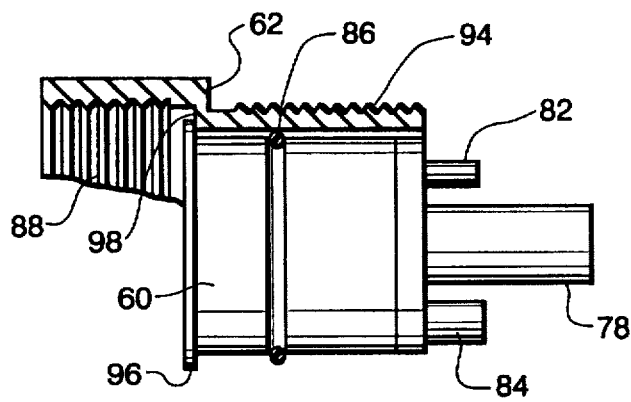
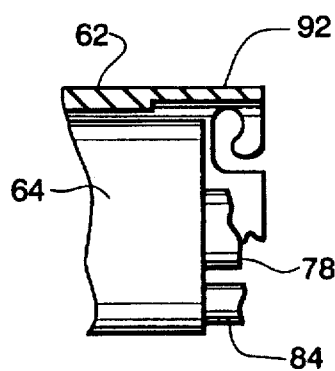
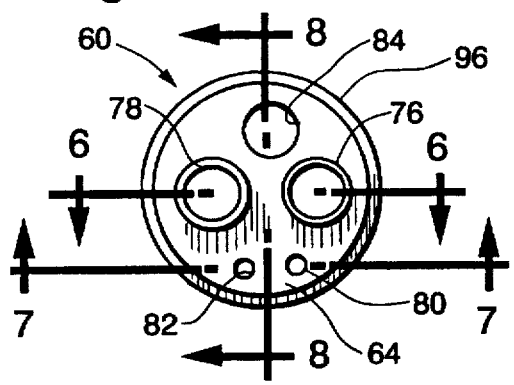
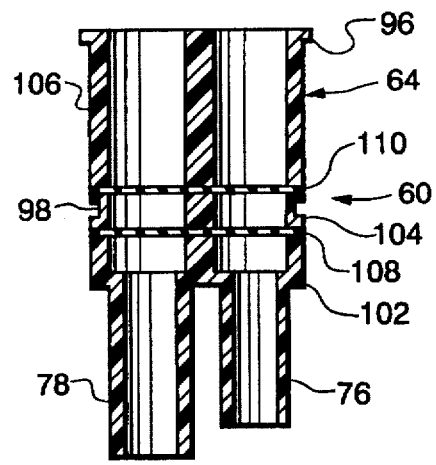
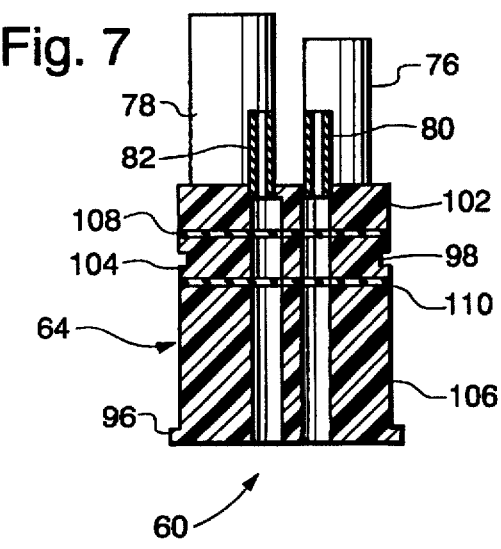
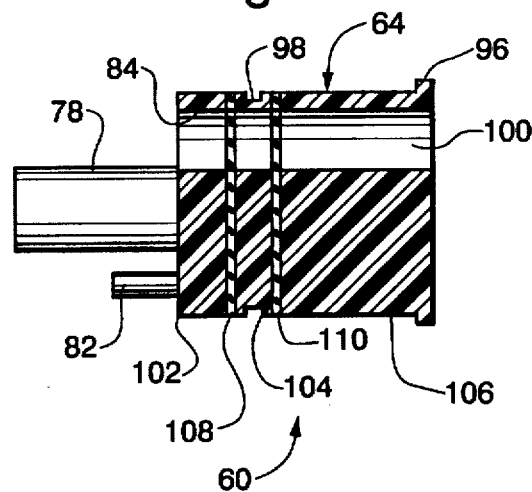

DISPOSABLE FILTER FOR DENTAL HANDPIECE

BACKGROUND OF THE INVENTION

The present invention is directed generally to improvements in dental devices and more particularly to a novel and improved filter for filtering respective air and water utility supplies to a hand-held dental device.

Many dental devices used by dentists utilize respective air and water supplies. Examples of such devices include handpieces (i.e., high speed dental drills), low speed air motors, syringes and scalers. Typically, such devices include a hand-held working portion with which some procedure is performed on the patient, and a utility supply portion, generally in the form of an elongate hose or tube through which air and water supplies to the hand-held portion are provided. The present application refers specifically to a high speed dental drill handpiece (hereinafter "handpiece") of the type which includes an air driven turbine for rotating a bur (i.e., the drill bit) for drilling the teeth of the patient.

Heretofore, the air and water supplied to the hand-held portion or handpiece of such dental devices has not been filtered. However, more recently there has been some concern regarding the presence of airborne and/or waterborne contaminants in this environment.

In a typical device from two (i.e., one air line and one water line) to four supply lines are provided in both the utility supply and in the hand-held portion. In a handpiece (high speed drill) these lines include a drive air line and an air exhaust line for driving a turbine portion of the handpiece. A water line is provided in such handpieces in order to cool the bur and the tooth of the patient so as to avoid overheating of the tooth. In this regard, typical rotational speeds of the burs of such handpieces are on the order of 400,000 rpm. It is generally preferred that the water supply be in a mist form, and to this end a secondary air line, often referred to as "chip air" is also often provided to mist the water from the water supply line as it leaves the handpiece. This chip air is provided in one of two forms. In some handpieces, the chip air is bled off from the drive air supply conduit while in other handpieces, a separate utility line is provided for chip air.

Many handpieces also include an optical opening through which a glass tube or fiber optic element is inserted to provide light near the working end of the handpiece. In some cases such light is provided in the form of a small electric lamp in the handpiece itself, in which case electrical connectors and conductors are provided in the handpiece and through the utility supply hose or tube. In other cases the lamp is provided near the end of the utility supply tube which carries appropriate electrical conductors and or connectors for the lamp, and the illumination from the lamp is fed through a fiber optic light conductor or other suitable conduit which extends through the handpiece portion of the device. In either event, provision for some sort of lighting requires the provision of an additional through opening or conduit in both the hand-held portion and the utility supply portion of the dental device, and alignment thereof.

Typically, such dental handpieces and their utility supply hoses or tubes are of relatively small diameter to facilitate easy grasping and maneuvering by the dentist. Accordingly, the space available within which to run the various supply lines or conduits, as well as the cross-sectional area available for providing filtering for these lines is limited. More particularly, it will be recognized that the cross-sectional areas or diameters of the respective air and water utility supplies and their corresponding openings or conduits in both handpiece and utility supply hose are smaller yet.

As an additional matter, it is currently recommended that a sterilized handpiece be used for each patient, thereby requiring that the handpiece be removed from the utility supply hose and replaced with a sterilized handpiece for each new patient. Under such circumstances, in order to maintain the sterile handpieces in a sterile condition, including the internal conduits for air and water, as well as to prevent cross-contamination of the utility supply hose or tube, we propose providing a filter intermediate the handheld portion and the utility supply portion of the dental device. We have further proposed filtering all of the supply lines which run from the utility supply to the band-held portion of the device, that is, not only the drive air but also the exhaust air, as well as the water and the chip air, in installations were a separate chip air line is provided in the utility supply.

Heretofore, handpieces have been connected to utility supply hoses in one of two manners. One type of connection is a threaded one in which a threaded coupling sleeve is used intermediate the handpiece and the supply hose. Either the handpiece has a plurality of tubes projecting longitudinally from its end part for insertion into corresponding mating openings in the supply hose, or vice-versa, to interconnect the respective lines for air and water, as described hereinabove. The handpiece and supply hose can also be coupled with a quick connect/disconnect type of coupling such as bayonet coupling of the type shown in prior U.S. Pat. No. 5,039,304, which is commonly owned herewith.

Therefore, the addition of a filter for the various air and water utilities to the handpiece must take into account the particular mating conduit end structures of the hand-held portion and supply hose, and also the mating coupling or connecting structures utilized in present dental devices. This is necessary in order to provide for retrofitting of a suitable filter to existing dental devices. Such considerations also apply at least in part to our proposed modified handpiece in which an additional end cavity portion is specifically provided for mounting such a filter element, such that the filter element will be interposed intermediate the air and water supply lines of the handpiece and of the utility supply hose in operation.

OBJECTS AND SUMMARY OF THE INVENTION

Accordingly, it is a general object of this invention to provide a novel and improved filter for a dental device.

Briefly, and in accordance with the foregoing, a filter is provided for a dental device of the type including a hand-held working portion which utilizes air and water and a utility supply portion which supplies air and water to said hand-held working portion through respective air and water conduits therein. The filter comprises a filter cartridge body defining an air opening running therethrough and a water opening running therethrough, said air and water openings being respectively positioned for alignment with corresponding air and water openings of one of a hand-held working portion and a utility supply portion; said filter cartridge having filtering means for respectively filtering air and water passing through the respective air and water openings thereof.

BRIEF DESCRIPTION OF THE DRAWINGS

The features of the present invention which are believed to be novel are set forth with particularity in the appended claims. The organization and manner of operation of the invention, together with further objects and advantages thereof may best be understood by reference to the following description, taken in connection with the accompanying drawings in which like reference numerals identify like elements, and in which:

FIG. 3 is a partial sectional view through a filter cartridge and adapter in accordance with one form of the invention;

FIG. 4 is a partial sectional view similar to FIG. 3 illustrating a bayonet type connection;

FIG. 5 is an end view of a filter cartridge in accordance with one form of the invention;

FIG. 6 is a sectional view taken generally along the line 6—6 of FIG. 5;

FIG. 7 is a sectional view taken generally along the line 7—7 of FIG. 5;

FIG. 8 is a sectional view taken generally along the line 8—8 of FIG. 5;

FIG. 9 is an enlarged partial sectional view similar to FIG. 7 showing an alternate form of a filter element in accordance with the invention; and FIG. 10 is an enlarged partial side elevation, partially in section, illustrating an assembled dental device similar to that of FIG. 1, including a modified filter in accordance with the invention.

DETAIL DESCRIPTION OF THE ILLUSTRATED EMBODIMENTS

Figure 1:
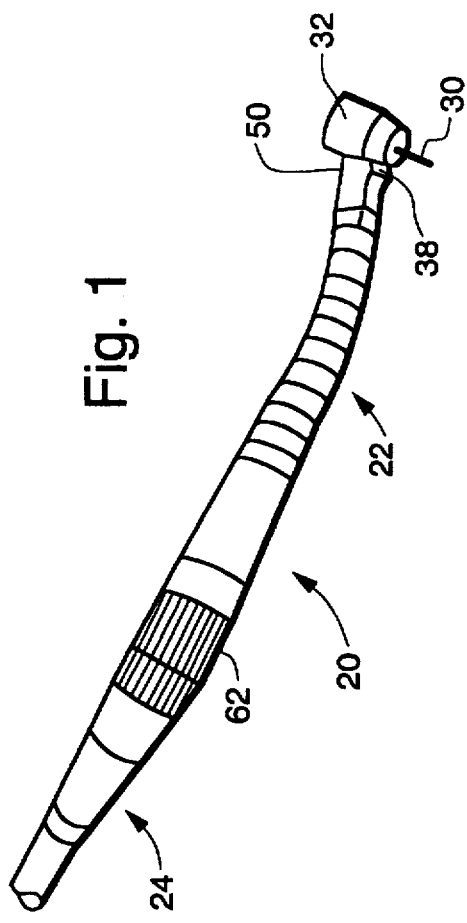
FIG. 1 is a perspective view of a dental device including a handpiece and utility supply hose, and provided with a filter in accordance with the invention.
Figure 2:
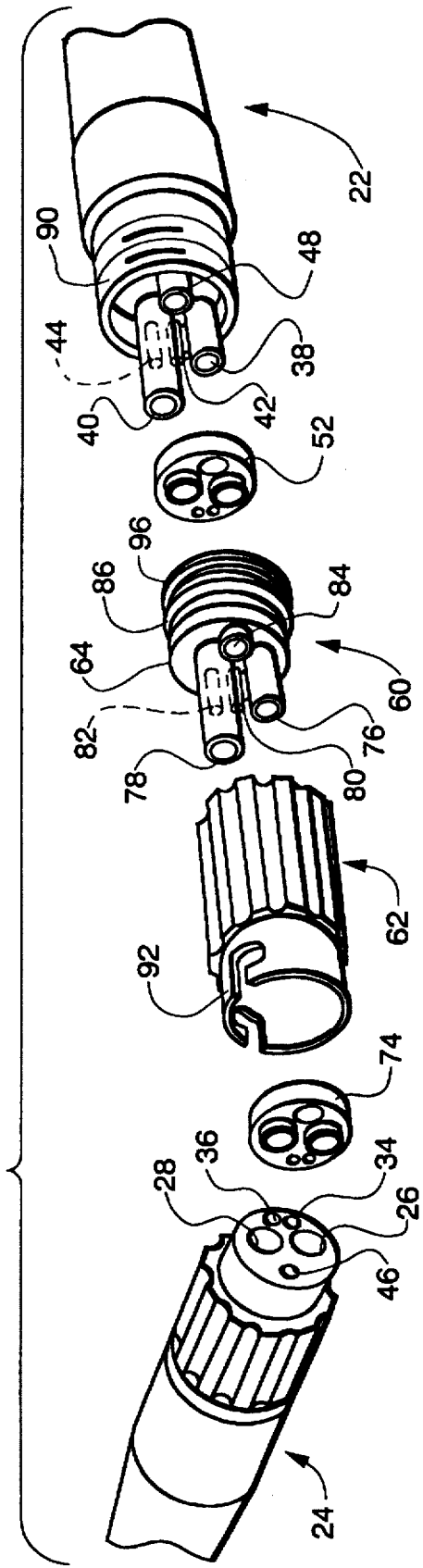
FIG. 2 is an enlarged partial exploded perspective view of the device of FIG. 1.

Referring now to the drawings, and initially to FIGS. 1 and 2, there is illustrated a dental device 20 of the type which includes a hand-held working portion 22 and a utility supply hose or tube portion 24 operatively coupled to the hand-held portion 22. In the illustrated embodiment the hand-held portion 22 comprises a high speed dental drill handpiece (hereinafter referred to as "handpiece"). The handpiece 22 receives both air and water supplies from the utility supply or hose 24. A hand-held working portion of a different sort, for example a low speed air motor, a syringe, or a scaler implement might be utilized with a similar utility supply 24 without departing from the invention.

The utility supply, as best seen in FIG. 2 includes elongated through tubes or conduits for supplying air and water respectively to the handpiece 22. In the illustrated embodiment, these air and water conduits include a drive air supply conduit 26 and an exhaust air conduit 28 for supplying air to and exhausting air from a turbine (not shown) which drives a bur 30 of the handpiece, this turbine being located in the head portion 32 of the handpiece 22. Water is provided for cooling the bur 30 and the tooth of the patient through a water supply conduit 34 and so-called chip air is provided through an air conduit 36. This chip air is used to mist or atomize the water, which has been supplied through the water conduit 34, at the head 32. In the handpiece 22 of FIG. 1 the water outlet is indicated generally at reference numeral 38 where it exits adjacent the head 32.

Similar conduits are provided within the handpiece 22 for matingly engaging the open ends of the conduits just described in the utility supply hose 24. These conduits generally project outwardly from the head so as to enter into the corresponding end openings of the hose conduits. These handpiece conduits include a drive air supply conduit 38, an exhaust air conduit 40, a water conduit 42 and a chip air conduit 44.

An additional optical opening or conduit is provided through which a fiber optic or other light source may be provided to illuminate the work area adjacent the head 32. This light conduit is indicated by reference numeral 46 in the hose 24 and by reference numeral 48 in the handpiece 22. The illumination is provided generally at a window or opening 50 adjacent the head 32 as shown in FIG. 1. A suitable sealing gasket 52 may be provided intermediate the handpiece 22 and the utility supply hose 24.

The above-described structure is generally similar to that illustrated and described in U.S. Pat. No. 5,039,305 which is commonly owned herewith, and in which the handpiece 22 directly couples to the utility supply hose 24 by means of a suitable adapter.

Departing from what is shown in this prior patent, the present invention advantageously interposes a filter cartridge 60 intermediate the handpiece 22 and the utility supply hose 24. In the embodiment illustrated herein the filter cartridge 60 is arranged to be held in an adapter 62, similar to the adapter shown in the above-reference patent, but lengthened somewhat in order to accommodate the filter cartridge 60. However, the filter cartridge 60 could be accommodated within a modified handpiece 22 or within a modified utility supply portion 24, without departing from the invention.

The filter cartridge 60 includes cartridge body 64 which includes a plurality of through conduits generally aligned with the respective air and water conduits of the handpiece 22 on the one side and of the utility supply hose 24 on the other side, these latter conduits having been described hereinabove. The filter cartridge 60 in the illustrated embodiment has air and water conduits which at one end are generally identical in form to the open ends of the conduits of the supply hose 24 and at the other end are generally identical in form to the projecting conduits of the handpiece 22, such that the filter cartridge 60 directly interfits between the handpiece 22 and supply hose 24. To this end, an additional gasket 74 substantially identical to gasket 52 is interposed between the supply hose and the filter cartridge 60, while the first gasket 52 is interposed between the filter cartridge 60 and the handpiece 22.

Referring also to FIGS. 3–8, the conduits of the filter cartridge 60 are identified as follows: drive air supply 76, exhaust air 78, water 80, chip air 82 and optical or light 84. An O-ring 86 is provided in the illustrated embodiment for sealing the exterior surface of the cartridge 60 with respect to a facing interior surface of the adapter 62, or of the handpiece 22, when a modified handpiece for accommodating the filter cartridge is provided, as mentioned above.

As shown in FIGS. 3 and 4, the adapter 62 is provided with suitable connectors at its ends for connection to the handpiece 22 on one side and to the supply hose 24 on the other side. The connector for connection to the handpiece 22 comprises an internally threaded surface 88 configured for mating engagement with an external thread 90 of the handpiece 22. In the embodiment illustrated in FIGS. 2 and 4, the connector for engagement with the supply hose 24 comprises quick connect or bayonet type connector 92. In this regard, the bayonet or quick connect type connector 92 and suitable mating pins (not shown) for engaging the same in the utility supply hose 24 are preferably as illustrated and described in the above-referenced U.S. Pat. No. 5,039,304. In the embodiment illustrated in FIG. 3, the adapter 62 includes a second externally threaded connector 94 for connection to a complementary thread (not shown) of a utility supply which is otherwise the same as the utility supply hose 24 illustrated in FIG. 2. In the illustrated embodiment, the cartridge body 60 also includes a somewhat enlarged diameter end portion 96 for engagement with a corresponding mating shoulder or step portion 98 formed within the adapter 62 for engaging and positioning the filter cartridge therewithin.

Referring now to FIGS. 5–10, the cartridge body 64 includes an annular circumferential groove 98 for accommodating the O-ring 86. As best viewed in FIG. 8, the light or optical conduit 48 comprises an elongate through opening through the cartridge body 64. An additional optical transmitting element such as a prism or fiber optic element 100 may be inserted in the opening 48 to enhance the transmission therethrough and through the filter cartridge, so as to minimize the light loss through the filter cartridge.

In the embodiment shown in FIGS. 5–9, the filter cartridge is composed of first, second and third body portions, 102, 104 and 106, each of which comprises a generally cylindrical body. These body portions 102, 104, 106 are coaxially aligned and of the same outer diameter in the preferred embodiment illustrated. The body portions 102, 104, 106 are spaced apart by narrow gaps, in which are fitted respective first and second filter elements 108, 110. The filter material selected for forming filter elements 108 and 110 will be of a selected porosity for excluding particles above a certain size. Various filter pore sizes might be selected in this regard, depending upon the type of viral, bacterial or other contaminants to be filtered.

Figures 9, 10:
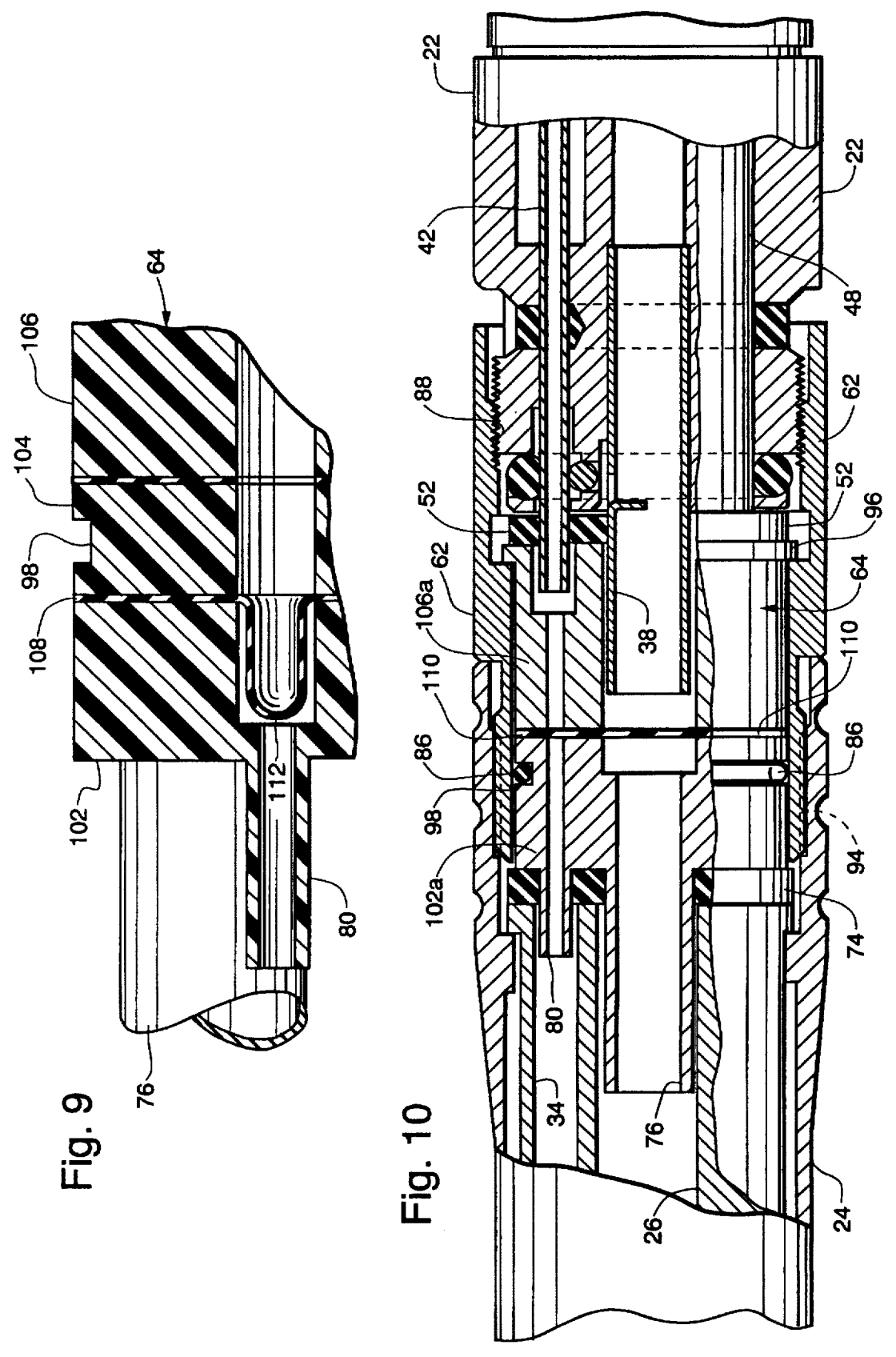

Referring briefly to FIG. 9, should an additional effective surface area of the filter be desired, an elongate tubular closed-ended portion of one or both filter elements might be formed extending into the conduit with which it is associated. One such extended tubular closed-ended portion of the filter element 108 is indicated at reference numeral 112 in FIG. 9, and extends into the conduit 42.

Fewer or more such filter elements and a corresponding number of body portions might be provided as desired without departing from the invention. For example, it is possible that one of the filter elements 108, 110 may serve to filter the water line while the other might serve to filter the three air lines or conduits. On the other hand, both of the filter elements 108 and 110 may extend across and filter all of the air and water lines or conduits, if desired in a particular application. In any event, all of the filter elements are provided with through openings through which the optical channel 84 and/or an optical element 100 contained therein may pass unimpeded as illustrated in FIG. 8.

In the embodiment shown in FIG. 10, a single filter, element 110 is positioned between two cartridge body portions 102a, 106a. It should be noted that the partial section shown in FIG. 10 is developmental in form, indicating a development or section which bisects the drive air supply conduit 76 and the water conduit 80. A portion of the optical conduit 48 of the handpiece 22 is also shown in FIG. 10, entering the filter cartridge 60.

In the illustrated embodiments, the body portions 102, 104 and 106 or 102a, 106a are generally coaxially aligned and have their outer circumferences or peripheries aligned. Similarly, the filter elements 108 and 110 preferably comprise relatively thin disk-shaped circular elements which are coaxially aligned with the filter cartridge body 64 and which have outer diameters sized the same as the outer diameter of the filter body 64 and its body portions 102, 104 and 106, or 102a and 106a. Thus, an external surface of the filter body is substantially continuous and cylindrical in form with the exception of the projecting holding portion 96 and the O-ring receiving groove 98. Also, the filter cartridge has smaller external cross-sectional dimensions than those of the handpiece 22 and utility hose 24. Accordingly, as shown in FIG. 1, the dental device incorporating the filter cartridge 60 operatively interposed between handpiece 22 and utility hose 24 is permitted a smooth merger of its external surfaces.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The Invention is claimed as follows:

1. A filter in combination with a dental device, said device including a handpiece having a hand-held working portion that includes a plurality of conduits for receiving and discharging water, air or light and a utility supply portion including conduits for supplying water, air and light to said working portion and receiving discharges therefrom, said filter comprising:

a filter cartridge including a cartridge body having a longitudinal axis and conduits for air, water or light running longitudinally through said cartridge body, said air and water openings being respectively positioned in alignment and register with the corresponding air, water and light conduits of said hand-held working portion and said utility supply portion, respectively;

at least one filter element comprising a relatively thin disc-shaped element extending transversely across said filter cartridge body, mounted within said filter cartridge and interposed across selected air, water or light conduits thereof for respectively filtering air water or light passing therethrough between the hand-held working portion and the utility supply portion of said dental device;

an adapter enclosing said filter cartridge therewithin, wherein all of said conduits in the working and supply portions and the filter cartridge of the dental device are in alignment and registered, said adapter including, sealing means whereby air, water or light are transmitted without leakage from said supply portion, through said filter cartridge body, to said hand-held working portion and connector means for sealingly connecting and mounting said adapter, with said filter cartridge body within, between said hand-held working portion and said utility supply portion of said dental device.

2. A filter according to claim 1 wherein said connector means include first connector means located and configured for cooperatively interfitting with a mating connector on a hand-held working portion of a dental device and second connector means located and configured for cooperatively interfitting with a mating connector on a utility supply portion of a dental device.

3. A filter according to claim 2 wherein said first and second connector means comprise threaded surfaces formed at opposite ends of the body of said adapter.

4. A filter according to claim 1 wherein said cartridge is configured for interfitting within a cavity provided therefor in a hand-held working portion of a dental device at an end thereof which is connectible to a utility supply portion.

5. A filter according to claim 1 wherein said filter element includes a generally tubular, closed-ended portion extending into at least one of said air and water openings in said filter cartridge body for increasing the effective surface area of said filter element.

6. A filter according to claim 1 and further including a second filter element comprising a relatively thin disc-shaped element extending transversely across said cartridge body and axially spaced from the first filter element.

7. A filter according to claim 1 wherein said cartridge body comprises first and second coaxially aligned body portions closely axially spaced for mounting said filter element therebetween.

8. A filter according to claim 1 wherein said cartridge body is smaller in cross-sectional dimensions than mating end parts of a hand-held portion and a utility supply portion of a dental device, to thereby permit a relatively smooth merger of external surfaces thereof with said filter cartridge operatively interposed therebetween.

9. A filter according to claim 1 wherein said cartridge body comprises a plurality of coaxially aligned, stacked body portions and wherein a plurality of filter elements are provided, each intermediate respective ones of said cartridge body portions.

10. A filter, in combination with a dental device of the type including (a) a hand-held working portion which utilizes air and water and (b) a utility supply portion which supplies air and water to said hand-held working portion through respective air and water conduits therein, said filter comprising:

a filter cartridge including a cartridge body having a longitudinal axis and air and water openings running longitudinally through said cartridge body, said air and water openings being respectively positioned for alignment with corresponding air and water openings of air and water conduits in facing ends of said hand-held working portion utility supply portion of the dental device; and at least one filter element mounted within said filter cartridge and interposed across at least one of the air and water openings thereof, filtering air or water passing therethrough between said hand-held working portion and said utility supply portion of the dental device, said filter cartridge being configured for mounting between said hand-held working and utility supply portions of said dental device, such that all of said openings are respectively in alignment, register and sealing connection, wherein said cartridge body further an elongate through opening for transmitting light from said utility supply portion to said hand-held working portion of the dental device.

11. A filter according to claim 10 and further including an optical transmitting element extending longitudinally through said elongate through opening of said cartridge body for transmitting light from a utility supply portion to a hand-held working portion of a dental device through said filter cartridge.

12. A filter according to claim 10 and further including a through opening in said filter element for transmitting light therethrough.

13. A dental device, comprising: a hand-held working portion including conduits for receiving and discharging air, water or light and a utility supply portion including conduits for supplying air, water or light to said hand-held working portion through respective air and water conduits therein;

a filter cartridge including a cartridge body having a longitudinal axis and air, water or light conduits running longitudinally through said cartridge body respectively positioned for alignment with corresponding air, water or light conduits in facing ends of said hand-held working portion and said utility supply portion, respectively;

at least one filter element mounted within said filter cartridge and interposed across the respective air and water openings thereof for respectively filtering air and water passing therethrough between said hand-held working portion and said utility supply portion;

adapter means having an adapter body configured for mounting said filter cartridge therewithin, wherein all of said conduits are in alignment and registered within said adapter whereby air, water or light are transmitted from said supply portion through said filter body to said hand-held working portion, said adapter means including sealing means to prevent leakage between conduits and a connector means for sealingly mounting said adapter, with said filter cartridge body within, intermediate said hand-held working portion and said utility supply portion of said dental device.

14. A dental device according to claim 13 wherein said cartridge is configured for interfitting within a cavity provided therefor in said hand-held working portion at an end thereof which is connectible to said utility supply portion.

15. A dental device according to claim 13 wherein said at least one filter element comprises a relatively thin disc-shaped element extending transversely across said filter cartridge body.

16. A dental device according to claim 15 and further including a second filter element comprising a relatively thin disc-shaped element extending transversely across said cartridge body and axially spaced from the at least one filter element.

17. A dental device according to claim 15 wherein said cartridge body comprises first and second coaxially aligned body portions closely axially spaced for mounting said at least one filter element therebetween.

18. A dental device according to claim 13 wherein said at least filter element includes a generally tubular, closed-ended portion extending into at least one of said air and water openings in said filter cartridge body for increasing the effective surface area of said filter element.

19. A dental device according to claim 13 wherein said cartridge body comprises a plurality of coaxially aligned, stacked body portions and wherein a plurality of filter elements are provided, each intermediate respective ones of said cartridge body portions.

20. A dental device according to claim 13 wherein said cartridge body has smaller cross-sectional dimensions than mating end parts of said hand-held portion and said utility supply portion to permit a smooth merger of external surfaces thereof with said filter cartridge operatively interposed therebetween.

21. A dental device, comprising: a hand-held working portion including conduits for receiving and discharging air, water or light and utility supply portion including conduits for supplying air, water or light to said hand-held working portion through respective air and water conduits therein;

a filter cartridge including a cartridge body having a longitudinal axis and air, water and light conduits running longitudinally through said cartridge body respectively positioned for alignment with corresponding air, water and light conduits of said hand-held working portion and said utility supply portion, respectively;

at least one filter element mounted within said filter cartridge and interposed across the respective air and water conduits thereof for respectively filtering air and water passing therethrough between said hand-held working portion and said utility supply portion;

an adapter configured for mounting said filter cartridge therewithin, wherein all of said conduits of said dental device are in sealing alignment or registered whereby air, water or light are transmitted from said supply portion through said filter cartridge to said hand-held working portion, said adapter further comprising connector means for sealingly mounting said adapter, said filter cartridge therewithin, intermediate said hand-held working portion and said utility supply portion of said dental device, wherein said cartridge body further includes an elongate through opening for transmitting light from said utility supply portion to said hand-held working portion.

22. A dental device according to claim 21 and further including an optical transmitting element extending longitudinally through said elongate through opening of said cartridge body for transmitting light from said utility supply portion to said hand-held working portion through said filter cartridge.

23. A dental device according to claim 21 and further including a through opening in said at least one filter element aligned with said through opening in said cartridge body.

24. A disposable filter in combination with a dental device that includes at least one conduit for receiving and discharging air or water and a supply line that includes at least one conduit for delivering air or water to said device and receiving any discharge therefrom, said filter comprising:

a cartridge body, interposed between said dental device and supply line, having at least one axial conduit therethrough coincident and in register with the conduits of said dental device and supply line, said cartridge body divided transversally into at least two body sections;

a filter element, relatively thin and disc-shaped, fitted to and extending transversally across and sandwiched between said cartridge body sections, said body sections supporting major surfaces of said filter element, said filter element filtering at least one conduit between said dental device and said supply line; and an adapter configured for sealably containing said filter cartridge body therein with all said air and water conduits between the dental device and supply line in alignment and register with those in the cartridge body, said adapter further including connector means for mounting said adapter, containing said disposable filter, between said dental device and said supply line.

25. A disposable filter for a dental device, including a handpiece that includes a plurality of conduits in combination with receiving and discharging air, water or light and a supply portion that includes conduits for delivering air, water or light to said handpiece and receiving discharge therefrom, said filter comprising:

a cartridge body interposable between said handpiece and supply portion having a plurality of conduits therethrough, coincident and in register with the plurality of conduits of said handpiece and supply portion, said cartridge body divided transversally into at least two body sections;

a filter element, relatively thin and disc-shaped, fitted to and extending transversally across and sandwiched between said cartridge body sections, said body sections supporting said filter element, said filter element partially obstructing at least one conduit for filtering and otherwise apertured to transmit air, water or light therethrough unobstructed; and an adapter configured for sealably containing said cartridge body therein with said conduits of the handpiece and supply portion in register and sealing contact with those in the cartridge body, said adapter further including connectors for mounting said adapter, containing said disposable filter, intermediate between said handpiece and said supply portion.

* * * * *